United States Patent
Iwata

(10) Patent No.: US 7,566,396 B2
(45) Date of Patent: Jul. 28, 2009

(54) FLOW PATH SWITCHING VALVE AND HIGH PERFORMANCE LIQUID CHROMATOGRAPH USING THE SAME

(75) Inventor: Yosuke Iwata, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 435 days.

(21) Appl. No.: 11/552,264

(22) Filed: Oct. 24, 2006

(65) Prior Publication Data
US 2007/0107499 A1    May 17, 2007

(30) Foreign Application Priority Data
Oct. 28, 2005    (JP) ............................. 2005-315399

(51) Int. Cl.
*B01D 15/08*    (2006.01)
(52) U.S. Cl. .................... 210/198.2; 210/659; 210/264; 137/625.46
(58) Field of Classification Search ................. 210/656, 210/659, 198.2, 264, 278, 284, 424, 425, 210/426; 137/625.11, 625.46
See application file for complete search history.

(56) References Cited

U.S. PATENT DOCUMENTS
4,705,627 A * 11/1987 Miwa et al. ................. 210/264

FOREIGN PATENT DOCUMENTS
JP    2003-202332    7/2003

OTHER PUBLICATIONS
PTO 09-5064 Translation of JP 2003-202332 May 2009.*

* cited by examiner

*Primary Examiner*—Ernest G Therkorn
(74) *Attorney, Agent, or Firm*—J.C. Patents

(57) ABSTRACT

The present invention is directed to reduce the dead volume in a flow path with trap functions. A flow path switching valve 1 is provided, which includes a rotor, i.e., rotor 3, and a housing top 9 having four ports 7a-7d connected to external flow paths, wherein two ports used for a mobile phase for analyzing are an inlet port 7a and an outlet port 7b, and the other two ports used for a mobile phase for condensing are an inlet port 7c and an outlet port 7d. In the rotor 3, two circular arc-shaped rotor trenches 11a, 11b for communicating two ports are formed at positions corresponding to the ports 7a-7d. The rotor trench 11b is filled with an adsorbent.

9 Claims, 4 Drawing Sheets

FLOW PATH SWITCHING VALVE AND HIGH PERFORMANCE LIQUID CHROMATOGRAPH USING THE SAME

CROSS-REFERENCE TO RELATED APPLICATION

This application claims the priority benefit of Japanese Patent Application No. JP 2005-315399, filed Oct. 28, 2005. All disclosure of the Japanese application is incorporated herein by reference.

BACKGROUND OF THE INVENTION

1. Field of Invention

The present invention relates to a high performance liquid chromatograph with trap functions like condensing sample components and a flow path switching valve used by the high performance liquid chromatograph with trap functions.

2. Description of Related Art

Among quality analyzers used for determining the structures of protein or peptide in the life science field, in order to optimize the measurement sensitivity, those involved in the art make great effects to minimize the flow of the high performance liquid chromatograph (HPLC) at the previous stage.

Generally, HPLCs for ordinary analysis operate by transmitting mobile phase at a flow speed of about 1 mL/min in a chromatographic column with an inner diameter of 4.6 mm. However, as for quality analyzers, micrometer HPLCs that transmit liquid at a flow speed of about 5 µL/min in a chromatographic column with an inner diameter of about 0.3 mm are generally adopted. In addition, nanometer HPLCs that transmit mobile phase at a flow speed of about 200 nL/min in a chromatographic column with an inner diameter of 0.075 mm have been commercialized.

When those extremely low-flow HPLCs are used for analysis, the object for being analyzed may be diffused due to the volume of the system (about 100 µL), thus affecting the sensitivity of the quality analyzer. Therefore, an auto-sampler or a manual injector is used to inject the object to be analyzed into the system. Next, the object to be analyzed is absorbed in the trap column mounted on the temporary flow path switching valve for being condensed. Then, the flow path switching valve is switched to transmit the mobile phase used for analyzing into the trap column. Thereafter, the above object to be analyzed is removed from the trap column, and then analyzed via an analytical column. Finally, the quality of the above object is analyzed by a quality analyzer.

The flow path switching valve employed in an extremely low-flow HPLC has a small inner volume due to the same reason as mentioned above. Generally, the main components of a flow path switching valve include a housing top for fixing the pipes that are led into the flow path switching valve, a rotor for switching flow paths through rotation, and a stator for keeping liquid-tight between the housing top and the rotor. In addition, the housing top may also serve as a stator occasionally.

FIG. 4A~4B show a conventional flow path switching valve. FIG. 4A is a general sectional view, and FIG. 4B is a general plan view.

The flow path switching valve 50 includes: a rotor for switching flow paths, i.e., rotor 53, a stator 55 contacting the rotor 53 to keep liquid-tight therebetween, and a housing top 59 for maintaining the stator 55 and having ports 51a-51f connected to external flow paths. The valve 50 is supported and driven by a valve supporting portion indicated by a dashed line. Among the ports 51a-51f, two ports used for the mobile phase for analyzing are an inlet port 51a and an outlet port 51b, another two ports used for the mobile phase for condensing are an inlet port 51c and an outlet port 51d, and the rest ports used for connecting the trap column 57 are ports 51e, 51f (referring to Japanese Patents Publication No. 01-307575, No. 09-288098).

SUMMARY OF THE INVENTION

In the flow path switching valve 50, the pipe led into the trap column 57 generally has an inner diameter of 25 µm, and a length of about 50 mm. If the inlet and the outlet are added together, the volume of the pipe is about 50 nL.

In addition, the pitch circle for forming the rotor trench of the rotor 53 has a length of 5 mm, a width of 0.1 mm, and a depth of about 0.1 mm, wherein the volume of the rotor trench is about 10 nL. Furthermore, the stator flow path has an inner diameter of 0.1 mm, a length of 1 mm, and a volume of about 15 nL. Therefore, the inner volume between two ports is about 25 nL, and the volume of the system becomes about 75 nL added with the volume of the pipe (50 nL).

When the volume of the system is 75 nL, if the flow rate of the valve is 200 nL/min, it takes about 20 seconds to pass between the flow path switching valve 50 and the trap column 57. However, during the above period, the analyzed object condensed by the trap column 57 is diffused, and thus sometimes, it is impossible to analyze the object by a quality analyzer with high sensitivity.

The present invention is directed to reduce the dead volume of the flow path with trap functions.

According to an embodiment of the present invention, the flow path switching valve comprises a housing top having a plurality of ports connected to the flow paths, and a rotor having rotor trenches disposed corresponding to the ports for communicating two ports. At least one of the rotor trenches is filled with an adsorbent, and the rotor is adhered to the housing top and is rotated, so as to switch the ports.

In order to reduce the dead volume within the valve, the housing top may also serves as a stator for keeping the rotation of the housing top and the rotor in a liquid-tight manner.

According to another embodiment of the present invention, the flow path switching valve comprises: a rotor having a plurality of rotor trenches for forming flow paths and serving as through holes, wherein at least one of the rotor trenches is filled with an adsorbent; a pair of housing tops, disposed facing each other for clamping the rotor, wherein ports connected to the flow paths are disposed corresponding to the rotor trenches. The connection between the two housing tops is switched by rotating the rotor.

Once trap functions are provided, at least six ports are required before, but now, four ports are enough.

The adsorbent is preferably the one with a monolith structure.

The HPLC of the present invention has the trap function of condensing the sample component selected via the flow path switching valve. The flow path switching valve used in the HPLC is the one provided by the present invention, and the adsorbent filled in the rotor trench serves as a trap.

EFFICACY OF INVENTION

The flow path switching valve of the present invention is used to communicate the rotor trenches filled with an adsorbent and switch the ports. Thus, so far, the pipe volume of about 50 nL required by the pipe between the flow path switching valve and the trap column and the volume of the rotor trench of about 10 nL become unnecessary. Therefore, the system only requires the volume within the housing top of 15 nL, thus reducing the dead volume. Thus, when the liquid is transmitted at a flow speed of 200 nL/min, it takes about 5 seconds to pass through the system, such that the diffusion of the analyzed object is restricted, and the time cost by the object to pass through the system is minimized.

If the housing top also serves as a stator for keeping the rotation of the rotor liquid-tight, the dead volume required by the inner volume of the stator can be further reduced.

If a pair of housing tops for clamping the rotor are provided, and the rotor trenches are in a direction parallel to the rotation direction of the rotor, the connection points for connecting the flow path switching valve to the pipe clamp the pair of housing tops in two sides, thus facilitating the connection at the connection points, and preventing liquid leakage when additional pipes are mounted.

So far, when the valve and the trap column are used for condensing, at least six ports are required. However, in the present invention, only four ports are needed, so as to miniaturize the flow path switching valve.

If the adsorbent is the one with a monolith structure, the adsorbent can be filled between the walls of the rotor trenches without any gap.

If the flow path switching valve of the present invention is applied to an HPLC with trap functions, the dead volume so far required by the pipe can be reduced in the HPLC.

BRIEF DESCRIPTION OF THE DRAWINGS

FIG. 1A~1D show a flow path switching valve according to an embodiment, wherein FIG. 1A is a perspective view of the flow path switching valve, FIG. 1B is a plan view of a housing top, FIG. 1C is a plan view of a rotor, and FIG. 1D is a sectional view of FIG. 1B along the Line X-X'.

FIG. 3A~3B show a flow path switching valve according to another embodiment, wherein FIG. 3A is a general sectional view and FIG. 3B is an exploded perspective view.

FIG. 4A~4B show a flow path switching valve that has been used so far, wherein FIG. 4A is a sectional view and FIG. 4B is a general plan view.

DESCRIPTION OF EMBODIMENTS

An embodiment of the present invention is described below in detail.

Figure 1A:
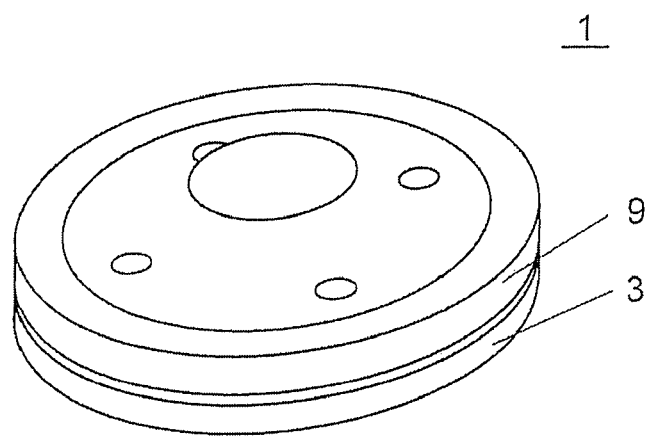
Figure 1B:
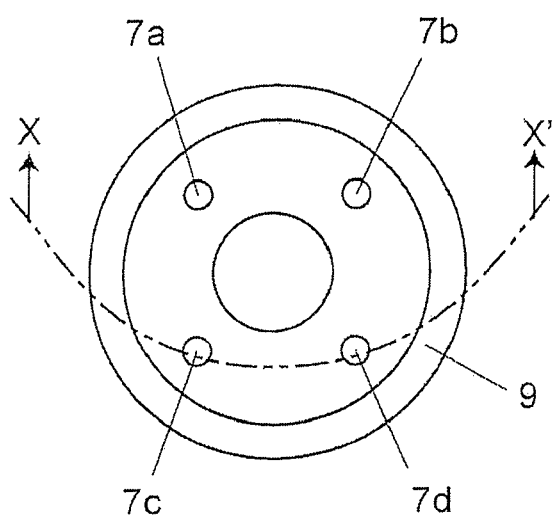
Figure 1C:
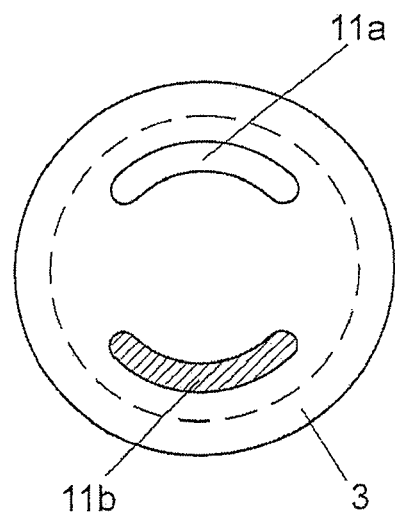
Figure 1D:
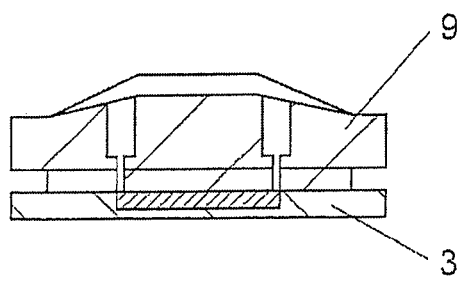

FIG. 1A~1D show a flow path switching valve, wherein FIG. 1A is a perspective view of the flow path switching valve, FIG. 1B is a plan view of a housing top, FIG. 1C is a plan view of a rotor, and FIG. 1D is a vertical sectional view of FIG. 1B along the Line X-X'. The flow path switching valve 1 includes: a rotor for switching the flow paths, i.e., rotor 3, and a housing top 9 having the stator function of keeping the rotation of the rotor 3 liquid-tight. In this embodiment, in order to reduce the volume of the value 1, the housing top 9 also serves as a stator.

In the housing top 9, four ports 7a-7d are disposed for being connected to external flow paths, wherein two of them used for the mobile phase for analyzing are an inlet port 7a and an outlet port 7b, and the other two used for the mobile phase for condensing are an inlet port 7c and an outlet port 7d.

On the surface opposite to the housing top 9 of the rotor 3, circular arc shaped rotor trenches 11a, 11b are formed at positions corresponding to the ports 7a-7d for communicating two ports. One pitch of the rotor trenches 11a, 11b has, for example, a radius of 2.5 mm, an interior angle of 90°, a width of 0.1 mm, and a depth of about 0.1 mm, and the volume thereof is about 40 nL. The rotor trenches 11a, 11b can be formed by, for example, mechanical processing.

An adsorbent functioning as a bulking agent is filled in the rotor trench 11b of the flow path switching valve 1, thus reducing the dead volume of the volume of the rotor trench or the pipe volume required so far for connecting the trap column with the external portion of the flow path switching valve.

In the trap column, the adsorbent such as particle-shaped silica gel ODS (Octadecylsilyl) with a particle diameter of about 5 μm is generally adopted, and the stainless steel or rubber is filled in the glass column. However, the adsorbent filled in the rotor trench 11b of the flow path switching valve 1 of the present invention is preferably monolith silica gel for integrating the three-dimensional network skeleton with the gaps thereof.

The monolith silica gel has a feature of a co-connection structure with the skeleton. The co-connection structure is a structure that is frozen with a transitional sequential structure generated by the phase separation via the hydrolysis-condensation polymerization reaction with sol-to-gel transitions, based upon the spinodal decomposition in the acetate aqueous solution of alkoxysilane and PEG.

The implementation of the same embodiment is illustrated below.

Each of the rotor trenches 11a, 11b of the rotor 3 forms an angle of 90° with respect to the central axis, such that the combination of the rotor trenches 11a, 11b and the ports 7a-7d can be switched by rotating the rotor 3 for 180°.

For example, if the rotor trench 11a is located between the ports 7a and 7b, and the rotor trench 11b is located between the ports 7c and 7d, once the rotor 3 is rotated for 180°, the rotor trench 11b is located between the ports 7a and 7b.

Figure 2:
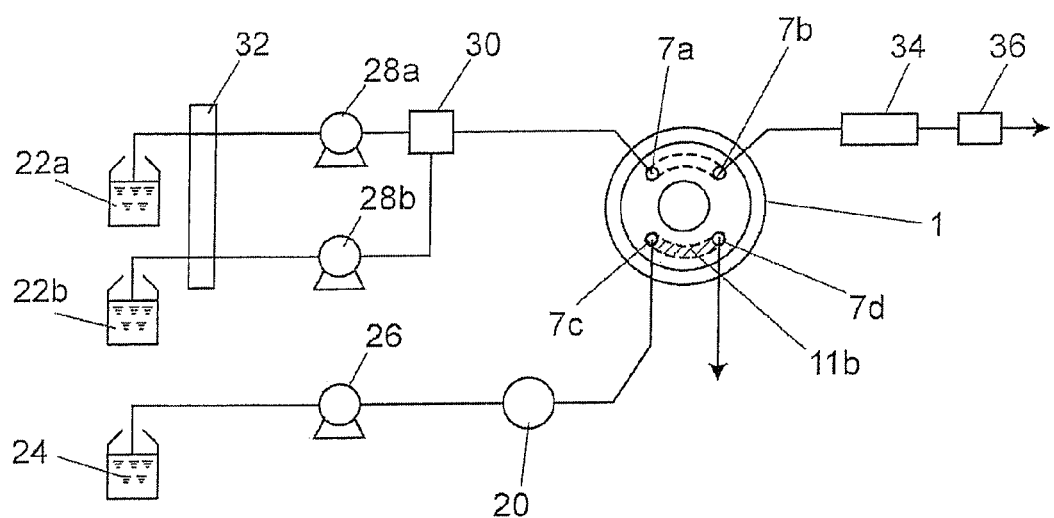
FIG. 2 is a flow path diagram of an embodiment of the HPLC using the flow path switching valve according to the same embodiment.

Then, FIG. 2 shows an embodiment of the HPLC using the flow path switching valve provided by the present invention.

In the extremely low-flow HPLC, in order to reduce the peak diffusion during the analysis mainly caused by the overall volume of the system due to the auto-sampler, the trap injection manner is adopted. That is, the sample to be injected into the system is transmitted by the auto-sampler through the mobile phase for condensing. Next, the condensing is conducted by the adsorbent filled in the rotor trench 11b in the flow path switching valve. Then, the flow path switching valve is switched to make the mobile phase for analyzing flow into the adsorbent in the rotor trench 11b, such that the samples condensed by the adsorbent are released, thus conducting the separation analysis via the analytical column.

In the HPLC of the present invention, the flow path switching valve 1 is connected to pumps for feeding liquids or to various mobile phases through the flow paths.

At the inlet port 7c of the mobile phase for condensing, a concentrate 24, a sample-carrying pump 26 for transmitting the concentrate 24, and an injection portion 20 for injecting samples via the auto-sampler are sequentially disposed from the upstream.

The outlet port 7d of the mobile phase for condensing is connected to a drain pipe.

At the inlet port 7a of the mobile phase for analyzing, mobile phases 22a, 22b for analyzing to melt out the captured components, a degasser 32 for removing the gas bubbles contained in the mobile phase, analytical pumps 28a, 28b for transmitting the mobile phases 22a, 22b for analyzing, and a stirrer 30 for mixing the mobile phases 22a, 22b for analyzing are sequentially disposed from the upstream. If the flow rate of the analytical pump 28a, 28b is controlled and the components of the mobile phase are altered, the gradient analysis can be conducted.

At the outlet port 7b of the mobile phase for analyzing, the analytical column 34 is connected to a detector 36.

The adsorbent for condensing is filled in the rotor trench 11b of the flow path switching valve 1, and the rotor is rotated, such that the connection of the rotor trench 11b is switched to the mobile phases 22a, 22b for analyzing, or to the condensate 24.

The operations of the same embodiment are illustrated below.

The samples are blood or urine of an animal or medicines that are administered with a component of an object to be detected, wherein the collected biological samples are centrifugally separated, so as to deposit the insoluble components. Next, the supernatant liquid is filtered via a filter till there is no problem in analyzing. After that, the sample is put into an auto-sampler to be analyzed. Alternatively, the biological samples can be directly placed into the auto-sampler to be analyzed.

[Condensing]

In FIG. 2, the condensate 24 is transmitted to the injection portion 20 from the pump 26. Next, the injection portion 20 sucks the sample from the sample bottle (not shown). Then, the sucked sample and the transmitted condensate 24 are simultaneously introduced into the flow path switching valve 1. Finally, the condensing is conducted by capturing the object components in the sample from the adsorbent in the rotor trench 11b.

[Analyzing after Condensing]

In FIG. 2, the mobile phases 22a, 22b for analyzing from the stirrer 30 are introduced into the flow path switching valve 1. At this time, the rotor 3 of the valve 1 is rotated for 180°. Next, through the introduced mobile phases 22a, 22b for analyzing, the components of the detected object captured in the adsorbent in the rotor trench 11b are melted out from the adsorbent, and then introduced into the analytical column 34 together with the mobile phases 22a, 22b for analyzing. Thus, various components are separated for being detected by the detector 36.

Figure 3A:
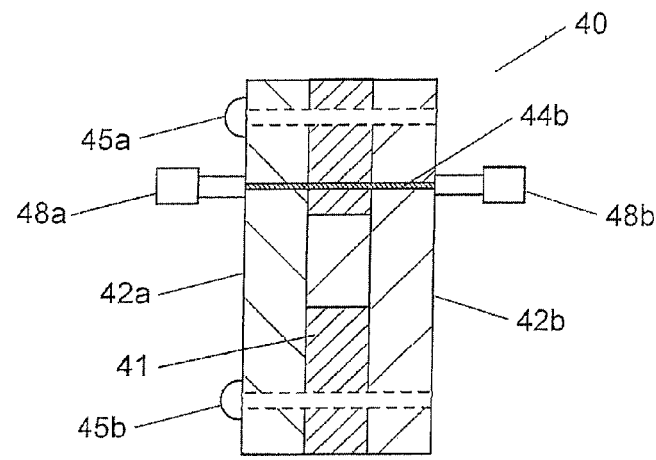
Figure 3B:
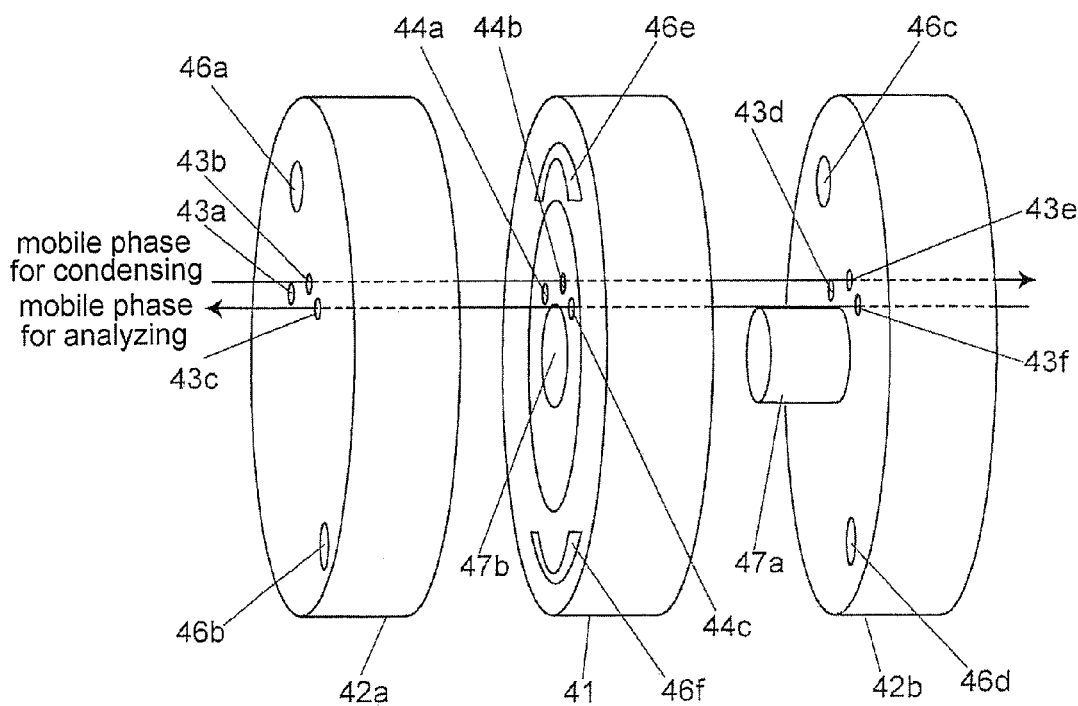
Figure 4A:
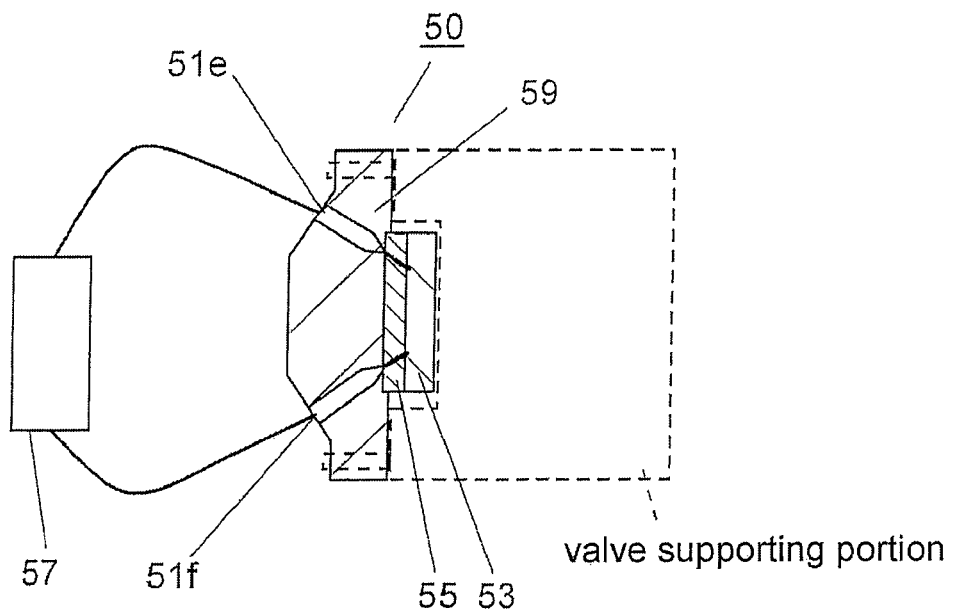
Figure 4B:
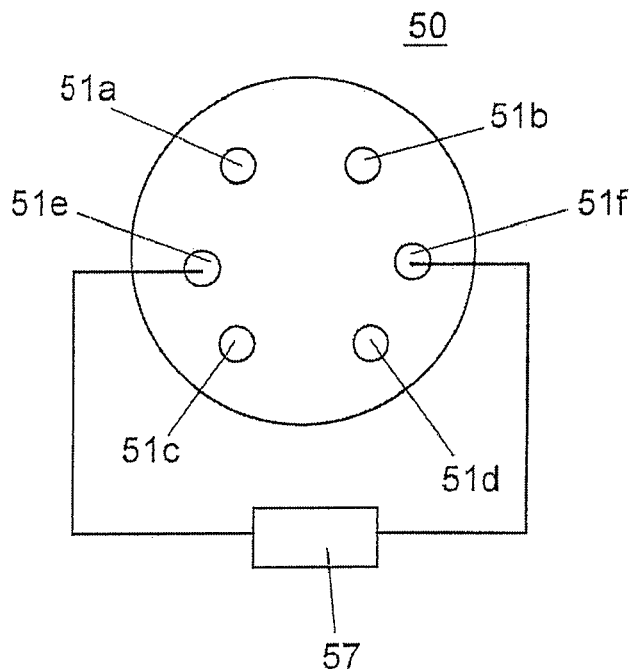

Then, FIG. 3A~3B show a flow path switching valve according to another embodiment of the present invention.

FIG. 3A is a general sectional view of the flow path switching valve, and FIG. 3B is an exploded perspective view.

The flow path switching valve 40 uses housing tops 42a, 42b to clamp the rotor (i.e., rotor 41) for switching the flow paths therebetween.

On the central axis of the housing top 42b, a cylindrical protrusion 47a is disposed for retaining the rotor 41 to be rotatable, and a through hole 47b embedded with the cylindrical protrusion 47a is disposed at the center of the rotor 41.

In the housing top 42a, three ports 43a-43c connected to the external flow paths are disposed, wherein two of them are an inlet port 43a of the mobile phase for analyzing and an outlet port 43b of the mobile phase for condensing. In the housing top 42b, three ports connected to the external flow paths are also disposed, wherein two of them are an outlet port 43d of the mobile phase for analyzing and an inlet port 43e of the mobile phase for condensing. The ports 43a-43c are respectively connected to the external flow paths via male nuts 48a, and the ports 43d-43f are respectively connected to the external flow paths via male nuts 48b.

In the rotor 41, the rotor through holes (rotor trenches) 44a-44c are formed for communicating the ports at the housing top 42a, with those at the housing top 42b. The rotor trench 44b filled with monolith silica gel mentioned in the above embodiment functions as an adsorbent.

In the housing tops 42a, 42b, through holes 46a, 46b and screw holes 46c, 46d are formed for the screws 45a, 45b to pass through. In the rotor 41, rotatable circular arc-shaped trench holes 46e, 46f are formed to avoid the screws 45a, 45b. By tightening the screws 45a, 45b, the rotor 41 is retained between the housing tops 42a, 42b in a rotatable state.

As such, the rotor through holes 44a-44c are maintained in a direction perpendicular to the rotation direction of the rotor 41, and the male nuts 48a, 48b are used to clamp the rotor 41 from the left and right sides, thereby enhancing the operability of the pipe. Accordingly, it becomes easier to process the tiny holes of the flow path entering the housing tops 42a, 42b, thus reducing the inner volume of the valve and reducing the processing cost of the housing top.

Next, the operations of the same embodiment are illustrated below.

The mobile phases for condensing are sequentially introduced to the port 43b, the rotor trench 44b, the port 44e, and then, the object components are captured via the adsorbent in the rotor trench 44b.

Afterward, the rotor trench 44b enables the rotor 41 to rotate until it reaches a position corresponding to a shaft connecting the ports 43c, 43f. Then, the mobile phases for analyzing are sequentially introduced into the port 43f, the rotor trench 44b and the port 43c, such that the components of the detected object are melted out of the adsorbent.

The present invention is not limited to the above embodiments, and can be implemented within the scope of the claims.

INDUSTRIAL AVAILABILITY

The present invention can be applied to flow path switching valves filled with an adsorbent.

LIST OF REFERENCE NUMERALS 1 flow path switching valve
3, 41 rotor
7a-7d, 43a-43f port
9, 42a, 42b housing top
11a, 11b, 44a-44c rotor trench
20 injection portion
22a, 22b mobile phase for analyzing
24 condensate
26 pump for feeding liquid
28a, 28b analytical pump
30 stirrer
32 degasser
34 analytical column
36 detector
45a, 45b screw

What is claimed is:

1. A flow path switching valve, comprising:
a housing top, having a plurality of ports connected to flow paths; and
a rotor, having two rotor trenches disposed at positions corresponding to the ports and used for communicating the ports, wherein at least one of the rotor trenches is filled with an adsorbent, and the rotor is adhered to and rotated with the housing top, so as to switch the ports.

2. The flow path switching valve as claimed in claim 1, wherein the housing top further serves as a stator for keeping the rotation of the housing top and the rotor in a liquid-tight manner.

3. The flow path switching valve as claimed in claim 1, wherein the flow path switching valve has four ports.

4. The flow path switching valve as claimed in claim 1, wherein the adsorbent has a monolith structure.

5. The flow path switching valve as claimed in claim 1, which is adaptable to a high performance liquid chromatograph (HPLC) having a trap for condensing a sample component selected via the flow path switching valve, wherein the adsorbent filled in the rotor trench serves as the trap.

6. A flow path switching valve, comprising:
   a rotor, having a plurality of rotor trenches for forming flow paths and serving as through holes, wherein at least one of the rotor trenches is filled with an adsorbent; and
   a pair of housing tops, disposed facing each other for clamping the rotor, and having ports connected to the flow path at positions corresponding to the rotor trenches,
   wherein the connections at the ports of the two housing tops are switched by rotating the rotor.

7. The flow path switching valve as claimed in claim 6, wherein the flow path switching valve has four ports.

8. The flow path switching valve as claimed in claim 6, wherein the adsorbent has a monolith structure.

9. The flow path switching valve as claimed in claim 6, which is adaptable to a high performance liquid chromatograph (HPLC) having a trap for condensing a sample component selected via the flow path switching valve, wherein the adsorbent filled in the rotor trench serves as the trap.

* * * * *